US010571195B2

(12) United States Patent
Yamamoto et al.

(10) Patent No.: US 10,571,195 B2
(45) Date of Patent: Feb. 25, 2020

(54) FURNACE MONITORING DEVICE AND GASIFICATION UNIT PROVIDED WITH SAME

(71) Applicant: MITSUBISHI HEAVY INDUSTRIES, LTD., Tokyo (JP)

(72) Inventors: Junichiro Yamamoto, Tokyo (JP); Tsutomu Kawamizu, Tokyo (JP); Takahiro Kubota, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 16/084,737

(22) PCT Filed: Dec. 1, 2016

(86) PCT No.: PCT/JP2016/085807
§ 371 (c)(1),
(2) Date: Sep. 13, 2018

(87) PCT Pub. No.: WO2017/168838
PCT Pub. Date: Oct. 5, 2017

(65) Prior Publication Data
US 2019/0072331 A1 Mar. 7, 2019

(30) Foreign Application Priority Data
Mar. 31, 2016 (JP) .................. 2016-071869

(51) Int. Cl.
*F27D 21/02* (2006.01)
*C10J 3/48* (2006.01)
*G01N 21/27* (2006.01)

(52) U.S. Cl.
CPC .............. *F27D 21/02* (2013.01); *C10J 3/48* (2013.01); *G01N 21/27* (2013.01);
(Continued)

(58) Field of Classification Search
CPC combination set(s) only.
See application file for complete search history.

(56) References Cited

U.S. PATENT DOCUMENTS 7,650,050 B2 * 1/2010 Haffner ................. B82Y 20/00
250/231.19
9,017,435 B2 4/2015 Leininger
(Continued)

FOREIGN PATENT DOCUMENTS

JP    H05-060473 A    3/1993
JP    H09-261516 A    10/1997
(Continued)

OTHER PUBLICATIONS

International Search Report dated Jan. 17, 2017, issued in counterpart application No. PCT/JP2016/085807, with English translation. (8 pages).
(Continued)

*Primary Examiner* — Kaity V Chandler
(74) *Attorney, Agent, or Firm* — Westerman, Hattori, Daniels & Adrian, LLC (57) ABSTRACT

A furnace monitoring device for monitoring the inside of a gasifier through which a combustible gas flows is provided with: a nozzle that has an internal cavity, and that is inserted inside the gasifier and fixed to the gasifier; a cylindrical protection tube which is inserted into the nozzle, and a part of which, located on the inside of the gasifier is, blocked; a monitoring window which is provided on the protection tube on the inside of the gasifier, and is made of a material that transmits light; a purge mechanism which supplies a gas containing an oxidizer to a surface of the monitoring window facing the inside of the gasifier; and an image capturing means which captures an image of the inside of the gasifier through the monitoring window.

4 Claims, 6 Drawing Sheets

(52) U.S. Cl.
CPC .............. *C10J 2300/0916* (2013.01); *C10J 2300/0956* (2013.01); *C10J 2300/12* (2013.01); *C10J 2300/18* (2013.01)

(56) References Cited

U.S. PATENT DOCUMENTS

| | | | | |
|---|---|---|---|---|
| 2004/0159773 | A1* | 8/2004 | Fein | ............... G01N 21/6458 250/208.1 |
| 2009/0153658 | A1* | 6/2009 | Saveliev | ............. H04N 5/2252 348/135 |
| 2009/0153853 | A1* | 6/2009 | Zelepouga | ............... G01J 3/02 356/300 |
| 2011/0261359 | A1* | 10/2011 | Inada | ............. H01L 31/035209 356/437 |
| 2014/0064445 | A1* | 3/2014 | Adler | ..................... G21K 7/00 378/43 |
| 2015/0286340 | A1* | 10/2015 | Send | ...................... G01S 17/46 345/175 |

FOREIGN PATENT DOCUMENTS

| | | | |
|---|---|---|---|
| JP | 2000-228732 | A | 8/2000 |
| JP | 2001-336735 | A | 12/2001 |
| JP | 2007-205708 | A | 8/2007 |
| JP | 4015354 | B2 | 11/2007 |
| JP | 2012-82419 | A | 4/2012 |

OTHER PUBLICATIONS

Written Opinion of International Searching Authority dated Jan. 17, 2017, issued in counterpart application No. PCT/JP2016/085807, with English translation. (13 pages).

* cited by examiner

FURNACE MONITORING DEVICE AND GASIFICATION UNIT PROVIDED WITH SAME

TECHNICAL FIELD

The present invention relates to a furnace monitoring device and a gasification unit provided with the same.

BACKGROUND ART

In the related art, as a gasification unit, a carbonaceous fuel gasification unit (gasification unit) is known, which supplies carbonaceous feedstock such as coal into a gasifier and partially combusts the carbonaceous feedstock to gasify the carbonaceous feedstock so as to generate a combustible gas. A furnace monitoring device for monitoring a situation in a furnace is provided in the gasification unit (for example, PTL 1).

PTL 1 discloses the furnace monitoring device including a cooling fluid passage which passes through an equipment housing portion housing a camera and a cleaning fluid passage which cleans a monitoring window which separates the inside of the furnace from the equipment housing portion. In the furnace monitoring device disclosed in PTL 1, air flows through the cooling fluid passage to cool an imaging device, and cleaning air or washing water blows from an ejection hole disposed at a tip of the cleaning fluid passage toward the monitoring window to clean the monitoring window.

CITATION LIST

Patent Literature (PTL 1) Japanese Patent No. 4015354

SUMMARY OF INVENTION

Technical Problem

Here, as described in PTL 1, in a case where the cleaning air blows to protect the monitoring window, if an oxygen containing gas such as oxygen is contained in the cleaning air, the cleaning air reacts with a combustible gas filling the inside of the gasifier, and thus, intense light is emitted. For this reason, there is a problem that a field of view of the furnace monitoring device is obstructed. In addition, in a case where the cleaning air is an inert gas, a solid in the furnace is solidified around the monitoring window and is accumulated around a monitoring region.

The present invention is made in consideration of the above-described problems, and an object thereof is to provide a furnace monitoring device capable of monitoring an inside of a furnace and a gasification unit provided with the same.

Solution to Problem

In order to solve the above-described problems, according to an aspect of the present invention, there is provided a furnace monitoring device which monitors an inside of a gasifier through which a combustible gas flows, including: a nozzle which is inserted into the gasifier, is fixed to the gasifier, and has an internal cavity; a protection tube which is formed in a tubular shape, is inserted into the nozzle, and has a blocked portion which is positioned inside the gasifier; a monitoring window which is provided on a portion of the protection tube inside the gasifier and transmits light; a purge mechanism which supplies a gas including an oxygen containing gas to a surface of the monitoring window inside the gasifier; and imaging means for imaging the inside of the gasifier via the monitoring window, in which the imaging means includes an imaging device which images the inside of the gasifier via the monitoring window, an optical filter which shields a wavelength of light emitted from a radical, and an optical filter switching unit which attaches the optical filter to the imaging device or detaches the optical filter from the imaging device.

According to this configuration, the optical filter which does not transmit the radical emission wavelength is attached to the imaging device, and thus, it possible to selectively shield the light from the radical emission to be incident on the imaging device, and thus, it is possible to monitor the inside of the gasifier even in a case where the radical emission is generated.

In addition, preferably, the optical filter transmits only a wavelength within a range from 759 nm to 928 nm.

According to this configuration, even in a case where an inside of a high-temperature gasifier filled with the combustible gas is purged by the gas including the oxygen containing gas, it is possible to prevent the emitted light of O2 radical and H2O radical from transmitting the optical filter and to monitor the inside of the gasifier with clearer images.

Moreover, preferably, the furnace monitoring device further includes control means which is connected to the optical filter switching unit, in which the control means attaches the optical filter to the imaging device in a case where a gas discharge temperature of the gasifier exceeds a preset value or a fuel is introduced into the gasifier, and the control means detaches the optical filter from the imaging device in a case where the gas discharge temperature of the gasifier is equal to or less than the preset value and the fuel is not introduced into the gasifier.

According to this configuration, in the case where the gasifier outlet gas thermometer exceeds the preset value or in the case where the burner inlet cutoff valve is opened, the control means controls the optical filter switching unit, and thus, the optical filter which does not transmit the radical emission wavelength is attached to the imaging device. Accordingly, it possible to selectively shield the light from the radical emission to be incident on the imaging device, and thus, it is possible to monitor the inside of the gasifier even in the case where the radical emission is generated.

According to this configuration, in the case where the gasifier outlet gas thermometer is equal to or less than the preset value or in the case where the burner inlet cutoff valve is closed, the control means controls the optical filter switching unit to detach the optical filter from the imaging device. Accordingly, it is possible to prevent luminance of the light incident on the imaging device from being decreased by the optical filter, and it is possible to monitor the inside of the gasifier even in a case where the luminance in the gasifier is not sufficient when the gasifier starts or stops.

In addition, preferably, the furnace monitoring device includes a lighting device which illuminates the inside of the gasifier via the monitoring window.

According to this configuration, it is possible to illuminate the inside of the gasifier, and it is possible to monitor the inside of the gasifier even in a case where the luminance in the gasifier is not sufficient when the gasifier starts or stops.

Moreover, preferably, the furnace monitoring device further includes a pressure resistance tube which is formed in a cylindrical shape and is inserted into the protection tube;

a transparent window which is provided on an end portion of the pressure resistance tube on the gasifier side to shield a space inside the protection tube and a space inside the pressure resistance tube and transmit light, a fiberscope which is accommodated in the pressure resistance tube, and a mirror which is disposed between the monitoring window and the transparent window and reflects light incident from the monitoring window to be incident on the transparent window, the monitoring window is formed on a side surface of a portion of the protection tube inserted into the gasifier, and the purge mechanism supplies the gas including the oxygen containing gas to a space between the protection tube and the pressure resistance tube, and blows out the gas including the oxygen containing gas from the monitoring window.

According to this configuration, the light incident from the monitoring window is reflected toward the fiberscope by the mirror, and the light incident on the fiberscope is transmitted to the lens of the imaging device by the fiberscope. Therefore, it is possible to image the inside of the gasifier from the side wall of the protection tube, it is possible to minimize an insertion depth of the protection tube, and a fluid friction generated between the gas flow inside the gasifier and the protection tube can be suppressed so as to be minimized. In addition, it is possible to transmit the light incident on the monitoring window from the inside of the gasifier to a location away from the gasifier such that a disposition position of the imaging device can be separated from the gasifier, it is possible to prevent the imaging device from being exposed to a high temperature, and a heat resistant temperature of the imaging device can be lowered.

In addition, preferably, the furnace monitoring device further includes a valve which is attached to the nozzle and shields the inside and an outside of the gasifier, a cylindrical vessel which is connected to the nozzle and shields a periphery of the protection tube from an outside; and a movement mechanism which moves the protection tube with respect to the cylindrical vessel.

According to this configuration, even in a case where trouble occurs in the furnace monitoring device during the operation of the gasification unit and maintenance is required, it is possible to attach the furnace monitoring device to the gasification unit or to detach the furnace monitoring device from the gasification unit without stopping the gasification unit, and it is possible to improve an operation rate of the gasification unit.

In addition, in order to solve the above-described problems, according to another aspect of the present invention, there is provided a gasification unit including any one of the above-described furnace monitoring devices.

Advantageous Effects of Invention

According to the present invention, it is possible to monitor the inside of the furnace even in a case where the inside of the high-temperature furnace filled with the combustible gas containing particles is purged by the gas including the oxygen containing gas.

DESCRIPTION OF EMBODIMENTS

Figure 1:
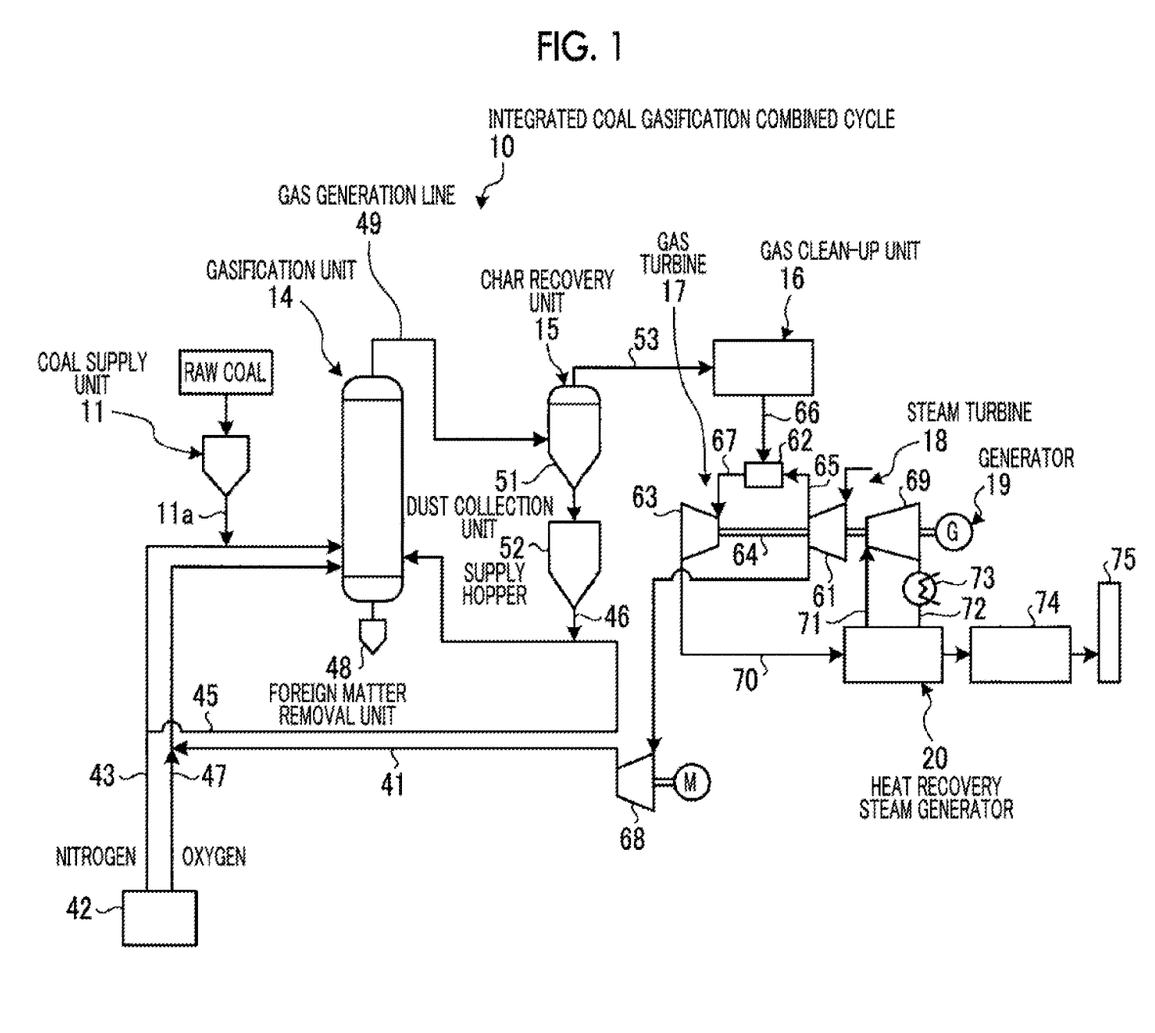
FIG. 1 is a schematic configuration diagram of an integrated coal gasification combined cycle to which a gasification unit according to a first embodiment is applied.
Figure 2:
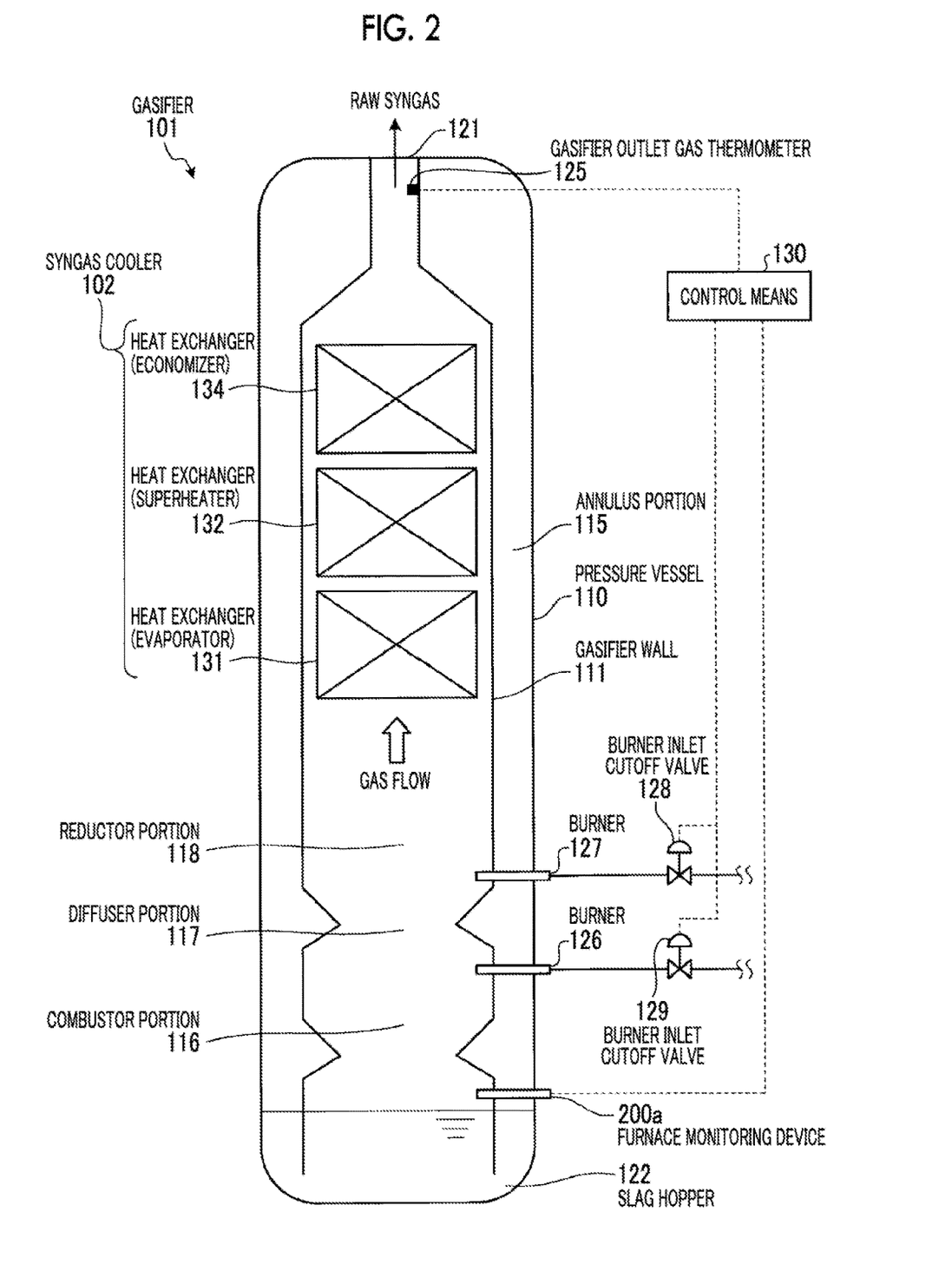
FIG. 2 is a schematic configuration diagram showing the gasification unit according to the first embodiment.
Figure 3:
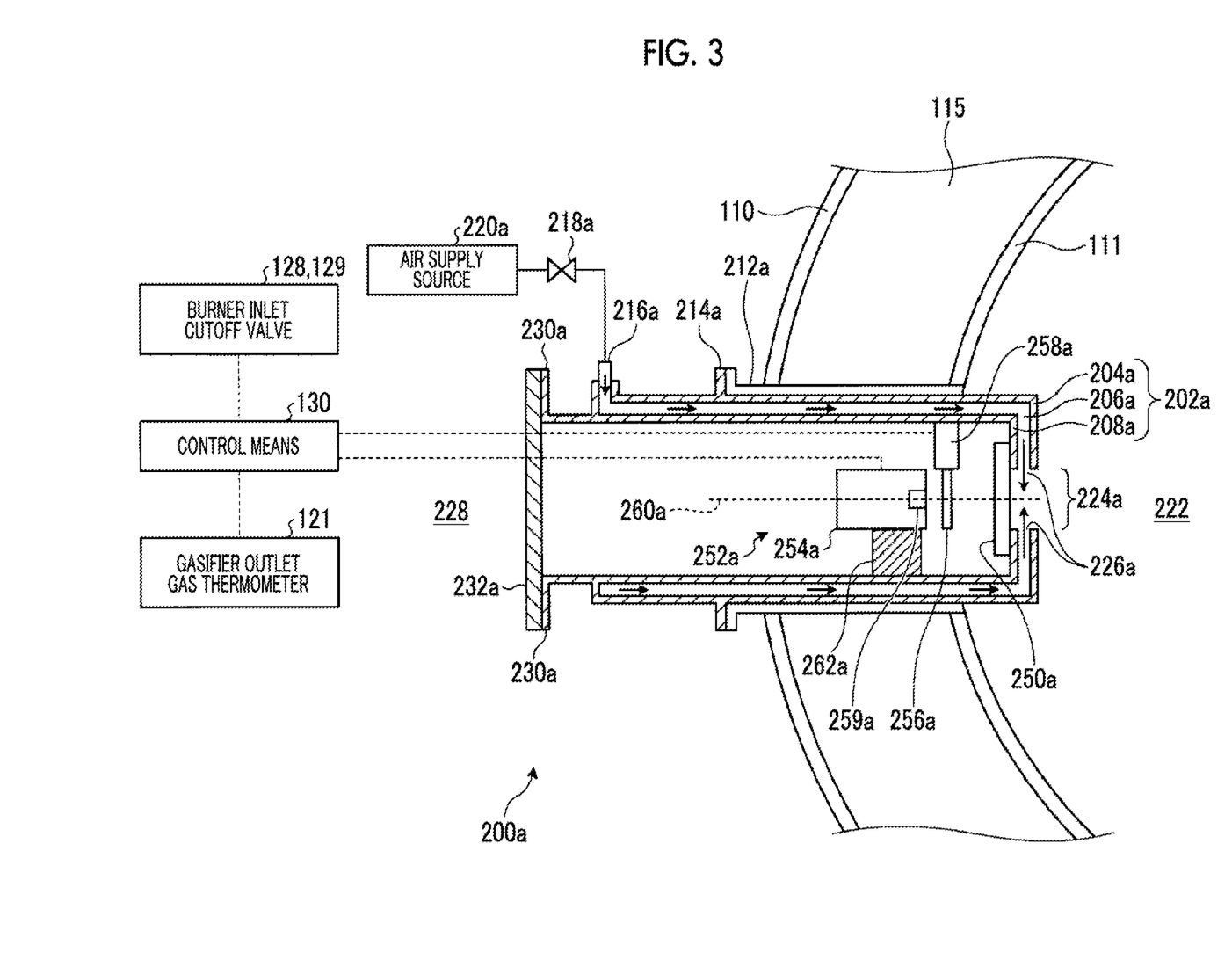
FIG. 3 is a cross-sectional diagram of a furnace monitoring device according to the first embodiment.

FIG. 1 is a schematic configuration diagram of an integrated coal gasification combined cycle to which a gasification unit according to a first embodiment is applied. FIG. 2 is a schematic configuration diagram showing the gasification unit according to the first embodiment. FIG. 3 is a cross-sectional diagram of a furnace monitoring device 200a according to the first embodiment.

In an integrated coal gasification combined cycle (IGCC) 10 to which a gasification unit 14 according to the present embodiment is applied, air is used as an oxygen containing gas, and the gasification unit 14 adopts an air combustion method which generates a combustible gas (raw syngas) from a fuel. In addition, in the integrated coal gasification combined cycle 10, the raw syngas generated by the gasification unit 14 is purified by a gas clean-up unit 16 to obtain a fuel gas, and thereafter, is supplied to a gas turbine 17 for power generation. That is, the integrated coal gasification combined cycle 10 of the first embodiment is an air combustion type (air blowing) power generating facility. For example, carbonaceous feedstock such as coal is used as the fuel supplied to the gasification unit 14.

As shown in FIG. 1, the integrated coal gasification combined cycle (integrated gasification combined cycle) 10 includes a coal supply unit 11, the gasification unit 14, a char recovery unit 15, the gas clean-up unit 16, the gas turbine 17, a steam turbine 18, a generator 19, and a heat recovery steam generator (HRSG) 20.

Coal which is carbonaceous feedstock as raw coal is supplied to the coal supply unit 11, and the coal supply unit II pulverizes the coal by a coal mill (not shown) or the like to produce pulverized coal pulverized into fine particles. The pulverized coal produced by the coal supply unit 11 is pressurized by a nitrogen gas serving as a carrier inert gas supplied from an air separation unit 42 to be described later at an outlet of the coal supply line 11a and is supplied to the gasification unit 14. The inert gas is an inert gas having an oxygen content of approximately 5 vol % or less, and a nitrogen gas, a carbon dioxide gas, an argon gas, or the like is representative as the inert gas. However, in the inert gas, the oxygen content is not necessarily limited to approximately 5% or less.

The pulverized coal produced by the coal supply unit 11 is supplied to the gasification unit 14, and a char (an unreacted portion and an ash content of the coal) recovered by the char recovery unit 15 is returned so as to be supplied reusably to the gasification unit 14.

In addition, a compressed air supply line 41 from the gas turbine 17 (compressor 61) is connected to the gasification unit 14, and thus, a portion of air compressed by the gas turbine 17 is boosted to a predetermined pressure by a booster 68 so as to be supplied to the gasification unit 14. The air separation unit 42 separates and generates nitrogen and oxygen from the air in the atmosphere, and the air separation unit 42 and the gasification unit 14 are connected to each other by a first nitrogen supply line 43. In addition, a coal supply line 11a from the coal supply unit 11 is connected to the first nitrogen supply line 43. Moreover, a second nitrogen supply line 45 branching off from the first nitrogen supply line 43 is also connected to the gasification unit 14, and a char return line 4 6 from the char recovery unit 15 is connected to the second nitrogen supply line 45. In addition, the air separation unit 42 is connected to the compressed air supply line 41 via the oxygen supply line 47. Moreover, nitrogen separated by the air separation unit 42 flows through the first nitrogen supply line 43 and the second nitrogen supply line 45 and thus, is used as a carrier gas of the coal or the char. In addition, oxygen separated by the air separation unit 42 flows through the oxygen supply line 47 and the compressed air supply line 41, and thus, is used as the oxygen containing gas in the gasification unit 14.

For example, the gasification unit 14 includes a two-stage entrained bed type gasifier 101 (refer to FIG. 2). In the gasification unit 14, the coal (pulverized coal) and the char supplied into the inside thereof are partially combusted by the oxygen containing gas (air and oxygen) to be gasified so as to be the raw syngas. In addition, the gasification unit 14 includes a foreign matter removal unit 48 which removes foreign matters (slag) mixed into the pulverized coal. In addition, a gas generation line 49 through which the raw syngas is supplied to the char recovery unit 15 is connected to the gasification unit 14, and the raw syngas including the char can be discharged from the gasification unit 14. As shown in FIG. 2, in this case, a syngas cooler 102 (gas cooler) may be provided in the gas generation line 49 such that the raw syngas is supplied to the char recovery unit 15 while being cooled to a predetermined temperature.

The char recovery unit 15 includes a dust collection unit 51 and a supply hopper 52. In this case, the dust collection unit 51 is configured of one or a plurality of cyclones or porous filters, and can separate the char contained in the raw syngas generated by the gasification unit 14. In addition, the raw syngas from which the char has been separated is fed to the gas clean-up unit 16 through a gas discharge line 53. The supply hopper 52 stores the char which is separated from the raw syngas by the dust collection unit 51. In addition, a bin may be disposed between the dust collection unit 51 and the supply hopper 52 such that a plurality of supply hoppers 52 are connected to the bin. In addition, the char return line 46 from the supply hopper 52 is connected to the second nitrogen supply line 45.

The gas clean-up unit 16 removes impurities such as sulfur compounds and nitrogen compounds from the raw syngas from which the char has been separated by the char recovery unit 15 so as to perform gas purification. In addition, the gas clean-up unit 16 purifies the raw syngas to produce the fuel gas and supplies the fuel gas to the gas turbine 17. In addition, a sulfur content (H2S, etc.) is still contained in the raw syngas from which the char has been separated, and thus, the gas clean-up unit 16 removes and recovers the sulfur content by using an amine absorbing solution and uses it effectively.

The gas turbine 17 includes the compressor 61, a combustor 62, and a turbine 63, and the compressor 61 and the turbine 63 are connected by a rotary shaft 64. The compressed air supply line 41 from the compressor 61 is connected to the combustor 62, a fuel gas supply line 66 from the gas clean-up unit 16 is connected to the combustor 62, and a combustion gas supply line 67 which extends toward the turbine 63 is connected to the combustor 62. In addition, the compressed air supply line 41 extending from the compressor 61 to the gasification unit 14 is provided in the gas turbine 17, and the booster 68 is provided in an intermediate portion of the compressed air supply line 41. Accordingly, in the combustor 62, a portion of the compressed air supplied from the compressor 61 and at least a portion of the fuel gas supplied from the gas clean-up unit 16 are mixed with each other to be combusted so as to generate a combustion gas, and the generated combustion gas is supplied to the turbine 63. In addition, in the turbine 63, the rotary shaft 64 is rotationally driven by the supplied combustion gas, and thus, the generator 19 is rotationally driven.

The steam turbine 18 includes a turbine 69 which is connected to the rotary shaft 64 of the gas turbine 17, and the generator 19 is connected to a base end portion of the rotary shaft 64. A flue gas line 70 from the gas turbine 17 (turbine 63) is connected to the heat recovery steam generator 20, and the heat recovery steam generator 20 performs heat exchange between supplied water and a flue gas of the turbine 63 so as to generate steam. In addition, a steam supply line 71 and a steam recovery line 72 are provided between the heat recovery steam generator 20 and the turbine 69 of the steam turbine 18, and a condenser 73 is provided in the steam recovery line 72. In addition, the steam generated by the heat recovery steam generator 20 may include the steam generated by the heat exchange with the raw syngas by the syngas cooler 102 of the gasifier 101. Accordingly, in the steam turbine 18, the turbine 69 is rotationally driven by the steam supplied from the heat recovery steam generator 20, the rotary shaft 64 is rotated, and thus, the generator 19 is rotationally driven.

In addition, a gas purifying unit 74 is provided from an outlet of the heat recovery steam generator 20 to a stack 75.

Here, an operation of the integrated coal gasification combined cycle 10 of the present embodiment will be described.

In the integrated coal gasification combined cycle 10 of the present embodiment, if the raw coal (coal) is supplied to the coal supply unit 11, the coal is pulverized into fine particles in the coal supply unit 11 so as to be the pulverized coal. The pulverized coal produced by the coal supply unit 11 flows through the first nitrogen supply line 43 by the nitrogen supplied from the air separation unit 42 so as to be supplied to gasification unit 14. In addition, the char recovered by the char recovery unit 15 described later flows through the second nitrogen supply line 45 by the nitrogen supplied from the air separation unit 42 so as to be supplied to the gasification unit 14. In addition, the compressed air bled from the gas turbine 17 described later is boosted by the booster 68, and thereafter, is supplied to the gasification unit 14 through the compressed air supply line 41 along with the oxygen supplied from the air separation unit 42.

In the gasification unit 14, the supplied pulverized coal and the char are combusted by the compressed air (oxygen), the pulverized coal and the char are gasified, and thus, the raw syngas is generated. In addition, the raw syngas is discharged through the gas generation line 49 from the gasification unit 14 and is fed to the char recovery unit 15.

In the char recovery unit 15, first, the raw syngas is supplied to the dust collection unit 51, and thus, fine char contained in the raw syngas is separated. In addition, the raw syngas from which the char has been separated is fed to the gas clean-up unit 16 through the gas discharge line 53. Meanwhile, the fine char separated from the raw syngas is accumulated in the supply hopper 52 and is returned to the gasification unit 14 through the char return line 46 so as to be recycled.

The gas clean-up unit 16 removes impurities such as sulfur compounds and nitrogen compounds from the raw syngas from which the char has beer, separated by the char recovery unit 15 so as to perform the gas purification, and thus, the fuel gas is produced. The compressor 61 generates the compressed air so as to supply to the combustor 62. The combustor 62 mixes the compressed air supplied from the compressor 61 and the fuel gas supplied from the gas clean-up unit 16 with each other and combusts the mixture to generate the combustion gas. The turbine 63 is rotationally driven by the combustion gas, and thus, rotationally drives the compressor 61 and the generator 19 via the rotary shaft 64. In this way, the gas turbine 17 can generate electricity.

Moreover, the heat recovery steam generator 20 performs heat exchange between the flue gas discharged from the turbine 63 and the supplied water in the gas turbine 17 so as to generate steam, and supplies the generated steam to the steam turbine 18. In the steam turbine 18, the turbine 69 is rotationally driven by the steam supplied from the heat recovery steam generator 20, and thus, the generator 19 is rotationally driven via the rotary shaft 64 so as to generate electricity.

In addition, the gas turbine 17 and the steam turbine 18 need not rotate and drive one generator 19 as the same shaft, and a plurality of generators may be rotationally driven by shafts different from each other.

Thereafter, in the gas purifying unit 74, harmful substances of an exhaust gas discharged from the heat recovery steam generator 20 are removed, and the purified exhaust gas is released from the stack 75 to the atmosphere.

Next, with reference to FIGS. 1 and 2, the gasification unit 14 in the integrated coal gasification combined cycle 10 will be described in detail.

As shown in FIG. 2, the gasification unit 14 includes the 101, the syngas cooler 102, a control means 130, and a furnace monitoring device 200*a*. The control means 130 has a function of a control means of the furnace monitoring device 200*a*.

The gasifier 101 is formed to extend in a vertical direction, and the pulverized coal and the oxygen are supplied to a lower side in the vertical direction so as to be partial combusted, and the gasified combustible gas (raw syngas) flows from the lower side in the vertical direction toward the upper side. The gasifier 101 includes a pressure vessel 110 and a gasifier wall 111 which is provided inside the pressure vessel 110. In addition, in the gasifier 101, an annulus portion 115 is formed in a space between the pressure vessel 110 and the gasifier wall 111. In addition, in the gasifier 101, in the space inside the gasifier wall 111, a combustor portion 116, a diffuser portion 117, and a reductor portion 118 are formed in this order from the lower side (that is, an upstream side in a flow direction of the raw syngas) in the vertical direction.

The pressure vessel 110 is formed in a tubular shape whose internal portion is a hollow space, a gas discharge port 121 is formed on an upper end portion of the pressure vessel 110, and a slag hopper 122 is formed on a lower end portion (bottom portion) thereof. A gasifier outlet gas thermometer 125 is disposed in in the gas discharge port 121. The gasifier wall 111 is formed in a tubular shape whose internal portion is a hollow space, and a wall surface of the gasifier wall 111 is provided to face an inner surface of the pressure vessel 110. Moreover, the gasifier wall 111 is connected to an inner surface of the pressure vessel 110 by a support member (not shown).

The gasifier wall 111 is formed by joining a heat transfer tube (not shown) and a fin (not shown) to each other by welding or the like. In addition, an upper end portion of the gasifier wall 111 is connected to the gas discharge port 121 of the pressure vessel 110, and a lower end portion of the gasifier wall 111 is provided with a gap between the lower end portion and a bottom portion of the pressure vessel 110. In addition, water is stored in the slag hopper 122 formed on a bottom portion of the pressure vessel 110, the stored water enters the lower end portion of the gasifier wall 111, and thus, the inside and the outside of the gasifier wall 111 are sealed.

The annulus portion 115 is a space which is formed inside the pressure vessel 110 and outside the gasifier wall 111, and the nitrogen which is an inert gas separated by the air separation unit 42 is supplied to the annulus portion 115 through a nitrogen supply line (not shown). Accordingly, the annulus portion 115 is a space which is filled with the nitrogen. In addition, a furnace internal pressure equalizing pipe (not shown) for equalizing the inside of the gasifier 101 is provided near the upper portion of the annulus portion 115 in the vertical direction. The furnace internal pressure equalizing pipe is provided to communicate with the inside and the outside of the gasifier wall 111 and equalizes the inside (combustor portion 116, diffuser portion 117, and reductor portion 118) and the outside (annulus portion 115) of the gasifier wall 111.

The combustor portion 116 is a space in which the pulverized coal, the char, and the air are partially combusted, and a combustion device configured of a plurality of burners 126 is disposed in the gasifier wall 111 in the combustor portion 116. The fuel is supplied to the plurality of burners 126 via a burner inlet cutoff valve 129. A portion of the pulverized coal and the char is partially combusted in the combustor portion 116, and thus, a generated high-temperature combustion gas passes through the diffuser portion 117 and flows into the reductor portion 118.

The reductor portion 118 is a space in which a high-temperature state required for a gasification reaction is maintained, the pulverized coal is supplied to the combustion gas from the combustor portion 116, and the pulverized coal is thermally decomposed into volatile components (carbon monoxide, hydrogen, lower hydrocarbon, or the like) to be gasified so as to generate the combustible gas. A combustion device configured of plurality of burners 127 is disposed in the gasifier wall 111 in the reductor portion 118. The fuel is supplied to the plurality of burners 127 via a burner inlet cutoff valve 128.

The syngas cooler 102 15 Provides inside the gasifier wall 111 and is provided vertically above the burner 127 of the reductor portion 118. In the syngas cooler 102, an evaporator 131, a superheater 132, and an economizer 134 are disposed in t is order from a vertically lower side (the upstream side in a flow direction of the raw syngas) of the gasifier wall 111. The syngas cooler 102 performs heat exchange with the raw syngas generated in the reductor portion 118 so as to cool the raw syngas. In addition, the evaporator 131, the superheater 132, and the economizer 134 are not limited to the number described in the drawing.

The control means 130 is connected to the gasifier outlet gas thermometer 125, the burner inlet cutoff valve 128, the burner inlet cutoff valve 129, and the furnace monitoring device 200*a* described later.

The furnace monitoring device 200*a* is a device which monitors the inside of the gasifier 101. The furnace monitoring device 200*a* will be described later.

Here, an operation of the gasification unit 14 of the above-described first embodiment will be described. In the gasifier 10*z* f the gasification unit 14, the nitrogen and the pi-liven-zed coal are injected and ignited by the burner 127 of the reductor portion 118, and the char and the compressed air (oxygen) are injected and ignited by the burner 125 of the combustor portion 116. Accordingly, in the combustor portion 116, the high-temperature combustion gas is generated by partial combustion of the pulverized coal and the char. In addition, in the combustor portion 116, a molten slag is generated in the high-temperature gas by the combustion of the pulverized coal and the char, and the molten slag is attached to the, gasifier wall 111, falls to a furnace bottom, and is finally discharged to the stored water in the slag hopper 122. In addition, the high-temperature combustion gas generated in the combustor portion 116 rises to the reductor portion 118 through the diffuser portion 117. In the reductor portion 118, a high-temperature state required for the gasification reaction is maintained, the pulverized coal is mixed with the high-temperature combustion gas, the pulverized coal is thermally decomposed into volatile components (carbon monoxide, hydrogen, lower hydrocarbons, or the like) in a high-temperature reducing atmosphere field so as to perform the gasification reaction, and thus, the combustible gas (raw syngas) is generated. The gasified combustible gas (raw syngas) flows from the lower side in the vertical direction toward the upper side.

In addition, in the above-described embodiment, the case where the gasification unit 14 is applied to the integrated coal gasification combined cycle 10 is described. However, the gasification unit 14 may be applied to a plant other than the integrated coal gasification combined cycle 10, for example, a gasifier of a garbage incineration plant and a gasifier of a chemical synthesis plant.

Moreover, in the above-described embodiment, the coal is used as the fuel. However, high rank coal and low rank coal can be used, and the fuel is not limited to the coal. That is, the fuel may be biomass which is used as a renewable organism-derived organic resource, and, for example, the fuel may be thinned wood, waste wood, driftwood, grasses, waste, sludge, tire, recycled fuel (pellets and chips) made from these as raw materials, or the like.

In addition, in the present embodiment, a tower type gasifier is described as the gasifier 101. However, even when the gasifier 101 is a crossover type gasifier, by replacing the upper side and the lower side in the vertical direction of each device in the gasifier 101 so as to match the gas flow direction of the raw syngas, the crossover type gasifier can be used.

Next, with reference to FIG. 3 in addition to FIG. 2, the furnace monitoring device 200a according to the first embodiment of the present invention will be described. The furnace monitoring device 200a includes a protection tube 202a, a nozzle 212a, a monitoring window 250a, imaging means 252a, and the control means 130.

The protection tube 202a is a cylindrical pipe which accommodates the imaging means 252a. The protection tube 202a includes an outer cylinder 204a, a fluid flow path 206a, an inner cylinder 208a, and an opening 224a. As shown in FIG. 3, the protection tube 202a is inserted into the nozzle 212a.

The nozzle 212a is a nozzle which is formed to penetrate the gasifier wall 111, the annulus portion 115, and a pressure vessel 110. The outer cylinder 204a is a cylindrical pipe. The outer cylinder 204a includes a flange portion 214a. The flange portion 214a is fixed to the nozzle 212a.

The fluid flow path 206a is a fluid flow path which is formed between the outer cylinder 204a and the inner cylinder 208a. As shown in FIG. 3, an ejection hole 226a is formed on an end portion of the fluid flow path 206a on the inside 222 of the furnace. As shown in FIG. 3, a boss 216a is formed on an end portion of the fluid flow path 206a on the outside 228 of the furnace. The boss 216a is connected to an air supply source 220a via the air source valve 218a. For example, the air supply source 220a is a compressor. The air supply source 220a supplies air to the fluid flow path 206a via an air source valve 218a and the boss 216a and ejects the air from the ejection hole 226a so as to perform purge.

The inner cylinder 208a includes a flange portion 230a on the outside 228 of the furnace. A closing flange 232a is attached to the flange portion 230a. As shown in FIG. 3, a support member 262a for fixing the imaging device 254a described later is fixed to the inner cylinder 208a. In addition, a fixing method is not particularly limited, and the support member 262a may be fixed by welding or may be fastened to be fixed by a bolt, a nut, or the like.

As shown in FIG. 3, the opening 224a is a circular opening which is formed at a center of a surface facing the protection tube 202a on the inside 222 of the furnace.

The monitoring window 250a is a window through which light is transmitted and includes the opening 224a. In the monitoring window 250a of the present embodiment, a transparent heat resistant member for transmitting light is disposed. The monitoring window 250a blocks the opening 224a with a transparent heat resistant member for transmitting light. For example, the transparent heat resistant member for transmitting light is a sapphire glass and a borosilicate glass. In the monitoring window 250a, an outer peripheral portion thereof which is in contact with the inner cylinder 200a is sealed, and thus, the inside of the gasifier 101 and the outside of the protection tube 202a are shielded.

The imaging means 252a includes an imaging device 254a, an optical filter 256a, an optical filter switching unit 258a, and a lighting device 259a. The imaging device 254a is a device which images the inside of the furnace via the monitoring window 250a. For example, the imaging device 254a is a CCD camera and a CMOS camera. The imaging device 254a is accommodated inside the protection tube 202a. The imaging device 254a includes a lens (not shown). As shown in FIG. 3, the imaging device 254a is fixed to the support member 262a such that an optical axis 260a of the lens (not shown) and the center of the opening 224a coincide with each other. The imaging device 254a outputs an image imaged by an output cable (not shown) to a monitor of a central control room (not shown). The imaging device 254a is connected to the control means 130.

The optical filter 256a is a filter which does not transmit a radical emission wavelength. Specifically, the radical emission wavelength is a wavelength included in the light emitted by radical in a case where a fuel containing carbon is combusted. For example, light emitted by CH radical has a band spectrum around 387 nm and 431 nm, and light emitted by O2 radical has a band spectrum near 759 nm. The optical filter 256a is larger than the lens of the imaging device 254a. That is, the optical filter 256a can cover the lens of the imaging device 254a in a case where the optical filter 256a is attached to the imaging device 254a. The optical filter 256a is fixed to the optical filter switching unit 258a.

As shown in FIG. 3, the optical filter switching unit 258a is fixed to the inner cylinder 208a. When the lens of the imaging device 254a is viewed via the monitoring window 250a from the inside 222 of the furnace, the optical filter switching unit 258a is an actuator which moves the optical filter 256a to a position at which the optical filter 256a covers the lens of the imaging device 254a or a position at which the optical filter 256a does not overlap the lens of the imaging device 254a. For example, the actuator is a servo motor. The optical filter switching unit 258a is connected to the control means 130.

As shown in FIG. 3, the lighting device 259a is fixed to the imaging device 254a. For example, the lighting device 259a is LED lighting. The lighting device 259a illuminates the inside of the furnace through the monitoring window 250a in an irradiation direction directed to the monitoring window 250a.

Here, an operation of the furnace monitoring device 200a of the above-described first embodiment will be described. In the furnace monitoring device 200a of the present embodiment, the air supply source 220a supplies air to the fluid flow path 206a via the air source valve 218a and the boss 216a so as to eject the air from the ejection hole 226a. The air ejected from the ejection hole 226a blows out particles attached to the monitoring window 250a and the particles filling the inside 222 of the furnace of the monitoring window. The air ejected from the ejection hole 226a reacts with the combustible gas filling the inside of the gasifier 101 and emits light.

In a case where the gasifier outlet gas thermometer 125 exceeds a preset value or in a case where the burner inlet cutoff valves 128 and 129 are opened, the control means 130 operates the optical filter switching unit 258a to attach the optical filter 256a to the imaging device 254a. Here, for example, the preset temperature is 1000° C. The optical-filter 256a shields an inner radical emission wavelength component of the light incident from the inside 222 of the furnace via the monitoring window 250a. That is, the optical filter 256a shields the radical emission wavelength component of the light generated by the reaction between the air ejected from the election hole 226a and the combustible gas. The imaging device 254a images light other than the radical emission wavelength transmitting the optical filter 256a.

In a case where the gasifier outlet gas thermometer 125 is equal to or less than a preset value or in a case where the burner inlet cutoff valves 128 and 129 are closed, the control means 130 operates the optical filter switching unit 258a to detach the optical filter 256a from the imaging device 254a. Here, for example, the preset temperature is 1000° C.

In the furnace monitoring device 200a according to the first embodiment, in the case where the gasifier outlet gas thermometer 125 exceeds the preset value or in the case where the burner inlet cutoff valves 128 and 129 are opened, the control means 130 controls the optical filter switching unit 258a, and thus, the optical filter 256a which does not transmit the radical emission wavelength is attached to the imaging device 254a. Accordingly, it possible to selectively shield the light from the radical emission to be incident on the imaging device 254a, and thus, it is possible to monitor the inside of the gasifier 101 even in a case where the radical emission is generated.

In the furnace monitoring device 200a according to the first embodiment, in the case where the gasifier outlet gas thermometer 125 is equal to or less than the preset value or in the case where the burner inlet cutoff valves 128 and 129 are closed, the control means 130 controls the optical filter switching unit 258a to detach the optical filter 256a from the imaging device 254a. Accordingly, it is possible to prevent luminance of the light incident on the imaging device 254a from being decreased by the optical filter 256a, and it is possible to monitor the inside of the furnace even in a case where the luminance in the gasifier 101 is not sufficient when the gasifier starts or stops.

The furnace monitoring device 200a according to the first embodiment includes the lighting device 259a. Accordingly, it is possible to illuminate the inside of the gasifier 101, and it is possible to monitor the inside of the furnace even in a case where the luminance in the gasifier 101 is not sufficient when the gasifier starts or stops.

It is preferable that the optical filter 256a is an optical filter which transmits light having a wavelength of 800 nm to 900 nm, and it is more preferable that the optical filter 256a is an optical filter which transmits light having a wavelength of 755 nm to 927 nm. Accordingly, even in a case where the inside of the high-temperature furnace filled with the combustible gas is purged by the gas including the oxygen containing gas, it is possible to prevent the emitted light of O2 radical and H2O radical from transmitting the optical filter 256a, it is possible to prevent a visual field of the imaging device 254a from being obstructed by the radical emission and to monitor the inside of the furnace with clearer images.

The optical filter 256a is an optical filter which does not transmit the radical emission wavelength. However, the optical filter 256a is an optical filter which transmits only the light having a wavelength from 700 nm to 1000 nm. Here, "to transmit only a selected wavelength range" may be a characteristic that substantially shields wavelengths other than the selected wavelength range, or may be a characteristic that cannot completely cut off the selected wavelength range and partially transmits the selected wavelength. The optical filter 256a is a filter which does not transmit the radical emission wavelength, and thus, even in the case where the inside of the high-temperature furnace filled with the combustible gas is purged by the gas including the oxygen containing gas, it is possible to prevent the light which includes a large amount of light generated by the radical emission and has the wavelength equal to or less than 700 nm from being transmitted to the optical filter 256a, and it is possible to prevent the visual field of the imaging device 254a from being obstructed by the radical emission and to monitor the inside of the furnace with clearer images. In addition, it is possible to selectively transmit the light which includes a large amount of light emitted by the gasifier wall 111 which is an object to be monitored and a particle flow and has the wavelength from 700 nm to 1000 nm, and it is possible to obtain the luminance required for imaging the object to be monitored by the imaging device 254a while shielding the light generated by the radical emission.

In addition, in the present embodiment, in the furnace monitoring device 200a, the air supply source 220a supplies the air. However, the present invention is not limited to this. The fluid supplied by the air supply source 220a may be a gas including the oxygen containing gas.

Moreover, in the present embodiment, in the furnace monitoring device 200a, the control means 130 controls the optical filter switching unit 258a so as to attach the optical filter 256a to the imaging device 254a or so as to detach the optical filter 256a from the imaging device 254a. However, the present invention is not limited to this. For example, the optical filter switching unit 258a may have a configuration in which the attachment and detachment of the optical filter 256a are performed by an operation of an operator.

In addition, in the furnace monitoring device 200a of the present embodiment, the optical filter 256a is attached to the imaging device 254a in the case where the gasifier outlet gas thermometer 125 exceeds the preset value or in the case where the burner inlet cutoff valves 128 and 129 are opened. However, the present invention is not limited to this. A condition for attaching the optical filter 256a may be any condition as long as the inside of the gasifier 101 has the luminance sufficient for imaging in the case where the optical filter 256a is attached to the imaging device 254a, and for example, a case where an outlet valve of the coal supply unit 11 is open may be adopted as the condition.

Moreover, the furnace monitoring device 200a of the present embodiment is provided in the gasification unit 14 of the integrated coal gasification combined cycle 10. However, the present invention is not limited to this. The furnace monitoring device 200a can be applied to any gasification unit as long as the combustible gas containing particles flows through the gasification unit. For example, the gasification unit through which the combustible gas containing particles flows is a gasification unit applied to a garbage incineration plant and a chemical synthesis plant.

Figure 4:
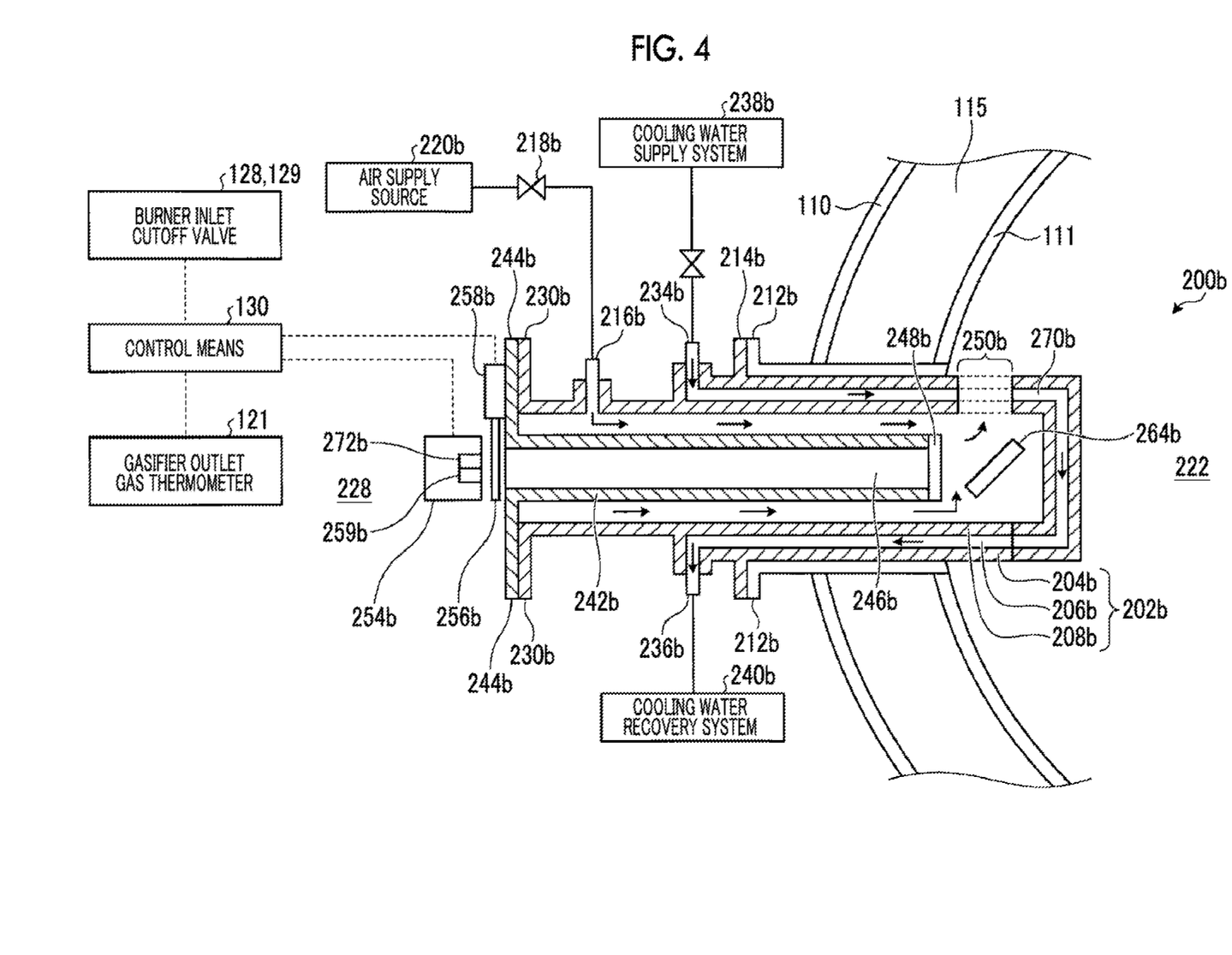
FIG. 4 is a cross-sectional diagram of a furnace monitoring device according to a second embodiment.
Figure 5:
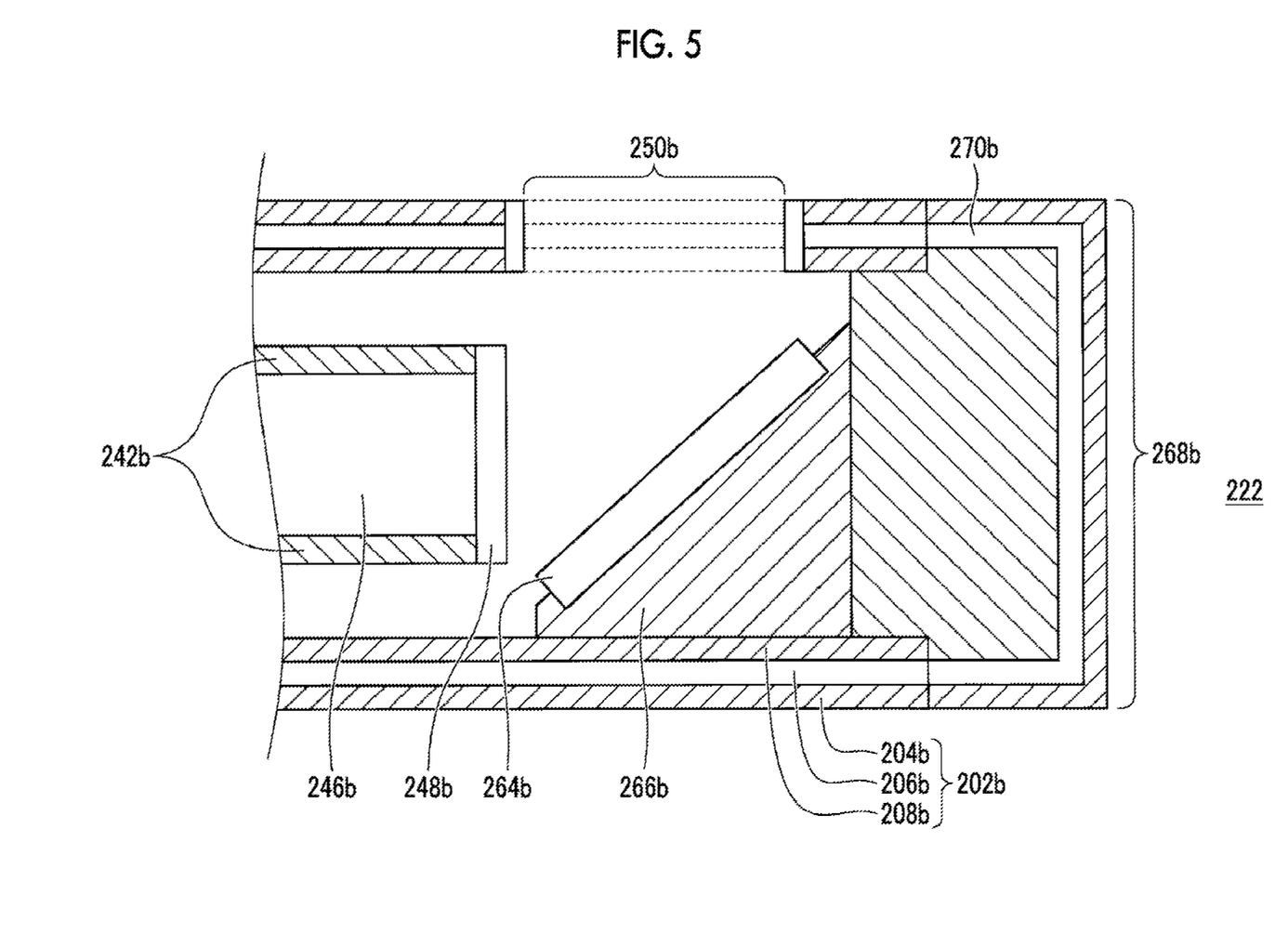
FIG. 5 is an enlarged diagram showing the furnace monitoring device according to the second embodiment in an enlarged manner.

Next, a furnace monitoring device 200b according to a second embodiment will be described with reference to FIGS. 4 and 5. FIG. 4 is a cross-sectional diagram of the furnace monitoring device according to the second embodiment. FIG. 5 is an enlarged diagram showing the furnace monitoring device according to the second embodiment in an enlarged manner. In addition, the furnace monitoring device 200b of the second embodiment can be applied to the gasification unit 14 instead of the furnace monitoring device 200a of the above-described first embodiment. That is, the gasification unit of the second embodiment has a configuration similar to that of the gasification unit 14 except for the furnace monitoring device 200b.

The furnace monitoring device 200b shown in FIGS. 4 and 5 includes a protection tube 202b, a fiber pressure resistance tube 242b, a fiberscope 246b, a monitoring window 250b, imaging means 252b, a mirror 264b, and a cap 268b.

The protection tube 202b is a cylindrical tube. The protection tube 202b includes an outer cylinder 204b, a fluid flow path 206b, and an inner cylinder 208b. As shown in FIG. 4, the protection tube 202b is inserted into a nozzle 212b. The nozzle 212b is a nozzle which is formed to penetrate the gasifier wall 111, the annulus portion 115, and the pressure vessel 110. The outer cylinder 204b is a cylindrical tube. The outer cylinder 204b includes a flange portion 214b. The flange portion 214b is fixed to the nozzle 212b.

The fluid flow path 206b is a flow path which is formed between the outer cylinder 204b and the inner cylinder 208b and through which cooling water flows. A boss 234b is connected to one end of the fluid flow path 206b and a boss 236b is connected to the other end thereof. The boss 234b is connected to a cooling water supply system 238b. The cooling water supply system 238b is a system which is connected to a cooling water cooling device (not shown) and supplies cooled cooling water. Here, for example, the cooling water cooling device is a cooling tower which causes the cooling water and the atmosphere to come into air-liquid contact with each other so as to cool the cooling water. The boss 236b is connected to a cooling water recovery system 240b. The cooling water recovery system 240b is a system which is connected to the cooling water cooling device (not shown) so as to feed the cooling water to the cooling water cooling device (not shown).

The inner cylinder 208b is a cylindrical tube. As shown in FIG. 4, a boss 216b is formed in the inner cylinder 208b. As shown in FIG. 4, the boss 216b is connected to a space described later which is surrounded by the fiber pressure resistance tube 242b, the transparent window 248b, and the inner cylinder 208b. The boss 216b is connected to an air supply source 220b via an air source valve 218b. For example, the air supply source 220b is a compressor. The air supply source 220b supplies the air to a space described later surrounded by the fiber pressure resistance tube 242b and the inner cylinder 208b via the air source valve 218b and the boss 216b, and ejects the air from the monitoring window 250b described later to the inside of the gasifier 101.

The fiber pressure resistance tube 242b is a cylindrical tube. The fiber pressure resistance tube 242b includes a flange portion 244b and a transparent window 248b. As shown in FIG. 4, the flange portion 244b is provided in the fiber pressure resistance tube 242b on the outside 228 of the furnace. The flange portion 244b is fixed to a flange portion 230b of the inner cylinder 208b.

The transparent window 248b is a window which is formed of a transparent heat resistant member transmitting the light. For example, the transparent heat resistant member transmitting the light is sapphire glass and borosilicate glass. The transparent window 248b is attached to the end portion of the fiber pressure resistance tube 242b on the inside 222 of the furnace. In the transparent window 248b, an outer periphery of a surface being in contact with the fiber pressure resistance tube 242b is sealed.

The fiberscope 246b is an industrial endoscope which transmits an image. As shown in FIG. 4, the fiberscope 246b is accommodated in the fiber pressure resistance tube 242b. The fiberscope 246b transmits the light incident from the transparent window 248b to an end portion of the fiber pressure resistance tube 242b on the outside 228 of the furnace.

As shown in FIG. 4, the monitoring window 250b is an opening which is formed in a portion inserted into the inside of the gasifier 101 in side surfaces of the protection tube 202b.

As shown in FIG. 5, the mirror 264b is fixed by a support member 266b in a direction in which the light incident from the monitoring window 250b is reflected by the fiberscope 246b.

The cap 268b is a cap which is attached to the end portion of the protection tube 202b on the inside 222 of the furnace. The cap 268b is fixed to the protection tube 202b. A fluid passage 270b through which the cooling water flows is formed inside the cap 268b. As shown in FIG. 5, in a case where the protection tube 202b and the cap 268b are connected to each other, both end portions of the fluid passage 270b are connected to both end portions of the fluid flow path 206b, and thus, a connected flow path of the cooling water is formed.

The imaging means 252b includes an imaging device 254b, an optical filter 256b, an optical filter switching unit 258b, a lighting device 259b, and an infrared thermometer 272b. The imaging device 254b is a device which images the inside of the furnace. For example, the imaging device 254b is a CCD camera and a CMOS camera. As shown in FIG. 4, the imaging device 254b is positioned at which the end portion of the fiberscope 246b on the outside 228 of the furnace and a lens (not shown) of the imaging device 254b face each other. The imaging device 254b has a recording function. The imaging device 254b outputs an image imaged by an output cable (not shown) to a monitor of a central control room (not shown). The imaging device 254b is connected to the control means 130.

The optical filter 256b is a filter which does not transmit a radical emission wavelength. Specifically, the radical emission wavelength is a wavelength included in the light emitted by radical in a case where a fuel containing carbon is combusted. For example, light emitted by CH radical has a band spectrum around 387 nm and 431 nm, and light emitted by O2 radical has a band spectrum near 759 nm. The optical filter 256b is larger than the lens of the imaging device 254b. That is, the optical filter 256b can cover the lens of the imaging device 254b in a case where the optical filter 256b is attached to the imaging device 254b. The optical filter 256b is fixed to the optical filter switching unit 258b.

As shown in FIG. 4, the optical filter switching unit 258b is fixed to the flange portion 244b of the fiber pressure resistance tube 242b on the outside 228 of the furnace. When the imaging device 254b is viewed from the end portion of the fiberscope 246b on the outside 228 of the furnace, the optical filter switching unit 258b is an actuator which moves the optical filter 256b to a position at which the optical filter 256a covers the lens of the imaging device 254a or a position at which the optical filter 256a does not overlap the lens of the imaging device 254a. For example, the actuator is a servo motor. The optical filter switching unit 258a is connected to the control means 130.

The lighting device 259b is provided in the imaging device 254b. For example, the lighting device 259a is LED lighting. The lighting device 259b illuminates the inside of the furnace via the fiberscope 246b. In addition, the lighting device 259b is provided in the imaging device 254b. However, the lighting device 259b may be provided on the end portion of the fiberscope 246b on the inside 222 of the furnace.

The infrared thermometer 272b is provided in the imaging device 254b. The infrared thermometer 272b measures a temperature inside the furnace via the fiberscope 246b.

Here, an operation of the furnace monitoring device 200b of the above-described second embodiment will be described. In the furnace monitoring device 200b of the present embodiment, the air supply source 220a supplies air to the space surrounded by the protection tube 202b and the fiber pressure resistance tube 242b via the air source valve 218b and the boss 216b so as to eject the air from the monitoring window 250b. The air ejected from the monitoring window 250b blows out particles attached to the monitoring window 250b and the particles filling the inside 222 of the furnace of the monitoring window. The air ejected from the monitoring window 250b reacts with the combustible gas filling the inside of the gasifier 101 and emits light.

The light incident from the monitoring window 250b is reflected toward the fiberscope 246b by the mirror 264b. The light incident on the fiberscope 246b is transmitted to the lens of the imaging device 254b by the fiberscope 246b.

In a case where the gasifier outlet gas thermometer 125 exceeds a preset value or in a case where the burner inlet cutoff valves 128 and 129 are opened, the control means 130 operates the optical filter switching unit 258b to attach the optical filter 256b to the imaging device 254b. Here, for example, the preset temperature is 1000° C. The optical filter 256b shields an inner radical emission wavelength component of the light incident from the inside 222 of the furnace via the monitoring window 250b. That is, the optical filter 256b shields the radical emission wavelength component included in the light generated by the reaction between the air elected from the monitoring window 250b and the combustible gas. The imaging device 254b images light other than the radical emission wavelength transmitting the optical filter 256b.

In a case where the gasifier outlet gas thermometer 125 is equal to or less than a preset value or in a case where the burner inlet cutoff valves 128 and 129 are closed, the control means 130 operates the optical filter switching unit 258b to detach the optical filter 256b from the imaging deli ice 254b. Here., for example, the preset temperature is 1000° C.

In the furnace monitoring device 200b according to the second embodiment, the light incident from the monitoring window 250b is reflected toward the fiberscope 246b by the mirror 264b, and the light incident on the fiberscope is transmitted to the lens of the imaging device 254b by the fiberscope 246b. Accordingly, it is possible to image the inside of the gasifier 101 from the side wall of the protection tube 202b, it is possible to minimize an insertion depth of the protection tube 202b, and a fluid friction generated between the gas flow inside the gasifier 101 and the protection tube 202b can be suppressed so as to be minimized. In addition, it is possible to transmit the light incident on the monitoring window 250b from the inside of the gasifier 101 to a location away from the gasifier 101 such that a disposition position of the imaging device 254b can be separated from the gasifier 101, it is possible to prevent the imaging device 254b from being exposed to a high temperature, and a heat resistant temperature of the imaging device 254b can be lowered.

The furnace monitoring device 200b of the second embodiment includes the infrared thermometer 272b. Accordingly, it is possible to measure the temperature of the gasifier wall 111, and in a gasifier which covers the gasifier wall 111 with a slag to protect the gasifier wall 111 from a high heat load, it is possible to detect of a change of the metal temperature of the gasifier wall 111, it is possible to detect a change in a thickness of the slag attached to the gasifier wall 111, and it is possible to estimate an accumulation rate of thermal fatigue of the gasifier wall 111 and to determine an inspection time of the gasifier 101.

In the furnace monitoring device 200b according to the second embodiment, the imaging device 254b has a recording function. Accordingly, it is possible to check a condition in the furnace in the past and to compare a current furnace condition with a past furnace condition, and in a gasifier which covers the gasifier wall 111 with a slag to protect the gasifier wall 111 from a high heat load, it is possible to monitor the change of an attachment condition of the slag, and it is possible to detect an abnormality of the gasifier wall 111.

In the furnace monitoring device 200b according to the second embodiment, the fluid flow path 206b is formed between the outer cylinder 204b and the inner cylinder 208b, and the cooling water flows through the fluid flow path 206b. Accordingly, it is possible to cool the inside of the protection tube 202b, it is possible to prevent the temperature of the imaging device 254b from increasing. and it is possible to protect the furnace monitoring device 200b from the high heat load of the gasification unit 14.

Preferably, a temperature of a purge gas supplied from the air supply source 220b is 100° C. or less, and more preferably, the temperature is 50° C. or less. Accordingly, it is more effectively cool the fiberscope 246b and the imaging means 252b.

Preferably, an ejection dynamic pressure in a case where the air supplied by the air supply source 220b is ejected from the monitoring window 250b is 100 Pa or more. In doing so, it is possible to effectively blow out the particles filling the inside of the gasifier 101, and thus, it is possible to secure the field of view of the imaging device 254b. In addition, even in a case where the inside of the furnace is in a high particle concentration atmosphere, it is possible to prevent the particles from entering the protection tube 202b.

Figure 6:
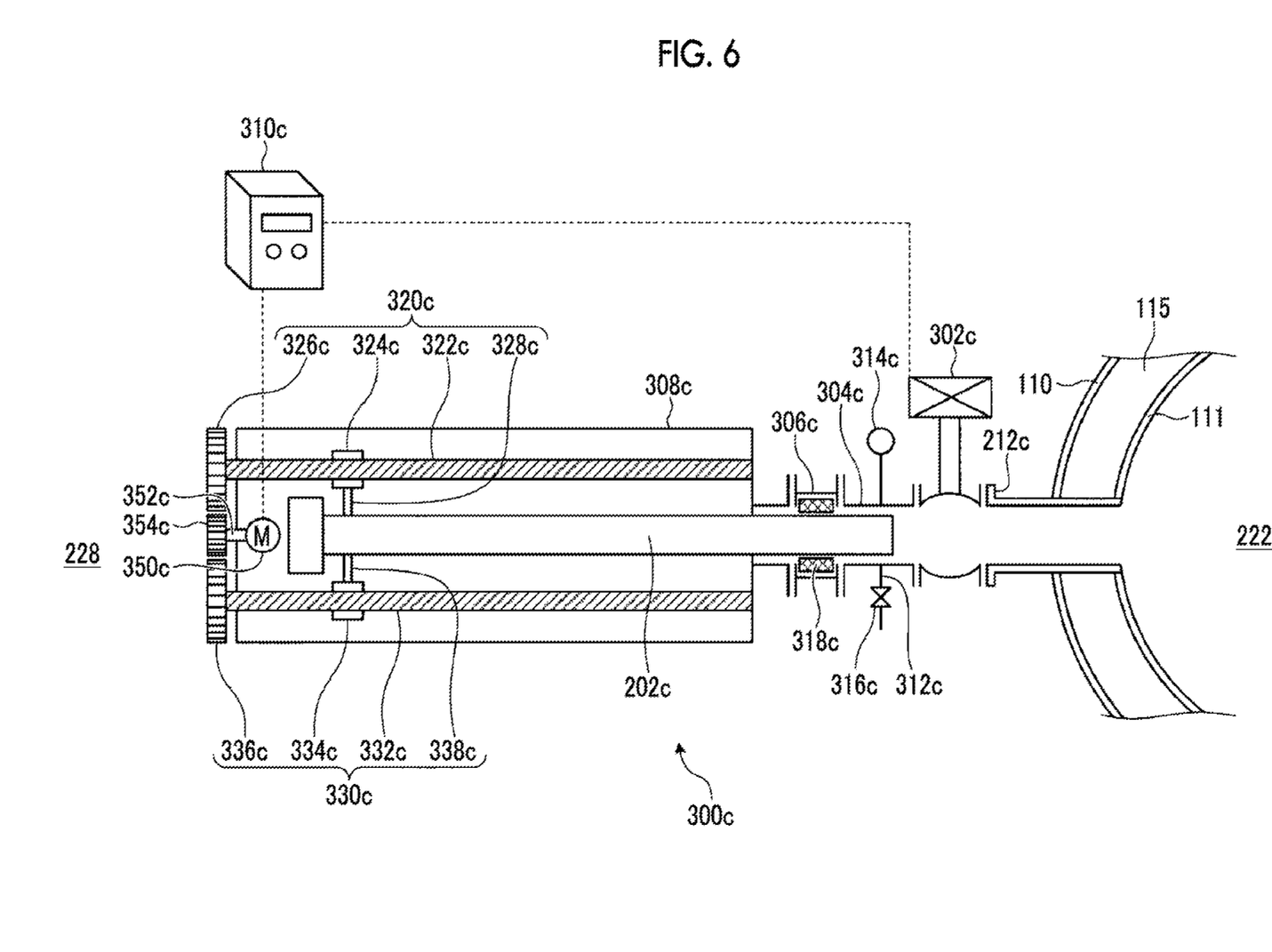
FIG. 6 is a cross-sectional diagram of a furnace monitoring device according to a third embodiment.

Next, a furnace monitoring device 200c of a third embodiment will be described with reference to FIG. 6. FIG. 6 is a cross-sectional diagram of the furnace monitoring device according to the third embodiment. In addition, the furnace monitoring device 200c of the third embodiment can be applied to the gasification unit 14 instead of the furnace monitoring device 200a of the above-described first embodiment. That is, the gasification unit of the third embodiment has a configuration similar to that of the gasification unit 14 except for the furnace monitoring device 200c. In addition, the furnace monitoring device 200c of the third embodiment is similar to the furnace monitoring device 200b of the second embodiment except for including an inserting and removing device 300c.

The inserting and removing device (movement mechanism) 300c includes a valve 302c, a first pipe 304c, a second pipe 306c, a cylindrical vessel 308c, an operation board 310c, a first ball screw mechanism 320c, a second ball screw mechanism 330c, and an electric motor 350c.

As shown in FIG. 6, the valve 302c is fixed to a portion between the nozzle 212c and the first pipe 304c by a bolt (not shown) and a nut (not shown). The valve 302c is an electric valve in which a motor (not shown) is housed. The valve 302c is connected to the operation board 310c. In a case where a close operation is input from the operation board 310c to the valve 302c, the valve 302c drives the motor (not shown) so as to shield a space inside the gasifier 101 and a space inside the first pipe 304c. In a case where an open operation is input from the operation board 310c to the valve 302c, the valve 302c drives the motor (not shown) to cause a space inside the gasifier 101 and a space inside the first pipe 304c to communicate with each other. In addition, the valve 302c is the electric valve. However, the present invention is not limited to this. For example, the valve 302c is a solenoid valve or a manual valve.

As shown in FIG. 6, the first pipe 304c is fixed to a portion between the valve 302c and the second pipe 306c using a bolt (not shown) and a nut (not shown). The first pipe 304c includes a depressurizing device 312c and a pressure gauge 314c. As shown in FIG. 6, the depressurizing device 312c is formed on a side surface of the first pipe 304c. The depressurizing device 312c is connected to the valve 316c. The depressurizing device 312c opens the valve 316c to cause the air in the first pipe 304c to flow and decreases the pressure in the first pipe 304c. As shown in FIG. 6, the pressure gauge 314c is formed on the side surface of the first pipe 304c. For example, the pressure gauge 314c is a Bourdon tube pressure gauge. The pressure gauge 314c measures the pressure inside the first pipe 304c.

As shown in FIG. 6, the second pipe 306c is fixed to a portion between the first pipe 304c and the cylindrical vessel 308c using a bolt (not shown) and a nut (not shown). A seal member 318c is provided inside the second pipe 306c. The seal member 318c is a member having a hollow columnar shape. As shown in FIG. 6, a protection tube 202c is inserted into a hollow portion of the seal member 318c. In a case where the protection tube 202c is inserted into the hollow portion, the seal member 318c shields the space inside the first pipe 304c and a space inside the cylindrical vessel 308c.

As shown in FIG. 6, the cylindrical vessel 308c is fixed to the second pipe 306c using a bolt (not shown) and a nut (not shown).

The first ball screw mechanism 320c includes a first screw shaft 322c, a first nut 324c, a first gear 326c, and a first support member 328c.

As shown in FIG. 6, one end of the first screw shaft 322c is rotatably supported by a side surface of the cylindrical vessel 308c on the inside 222 of the furnace, and the other end thereof is rotatably supported in a state of penetrating a side surface of the cylindrical vessel 303c on the outside 228 of the furnace. The first nut 324c is rotatably attached to the first screw shaft 322c. The first gear 326c is fixed to an end portion of the first screw shaft 322c on the outside 228 of the furnace. As shown in FIG. 6, one end of the first support member 328c is fixed to the first nut 324c and the other end thereof is fixed to the protection tube 202c.

The second ball screw mechanism 330c includes a second screw shaft 332c, a second nut 334c, a second gear 336c, and a second support member 338c.

As shown in FIG. 6, one end of the second screw shaft 332c is rotatably supported by a side surface of the cylindrical vessel 308c on the inside 222 of the furnace, and the other end thereof is rotatably supported in a state of penetrating a side surface of the cylindrical vessel 308c on the outside 223 of the furnace. The second nut 334c is rotatably attached to the second screw shaft 332c. The second gear 336c is fixed to an end portion of the second screw shaft 332c on the outside 228 of the furnace. As shown in FIG. 6, one end of the second support member 338c is fixed to the second nut 334c and the other end thereof is fixed to the protection tube 202c.

A shaft 352c is connected to the electric motor 350c. As shown in FIG. 6, the shaft 352c is rotatably fixed to a side surface of the cylindrical vessel 308c on the outside 228 of the furnace. A third gear 354c is attached to a tip of the shaft 352c. As shown in FIG. 6, the third gear 354c is disposed between the first gear 326c and the second gear 336c such that these gears mesh with each other. The electric motor 350c is connected to the operation board 310c. In a case where an operation for inserting the protection tube 202c is input from the operation board 310c to the electric motor 350c, the electric motor 350c is rotated in a direction in which the protection tube 202c is moved to the inside 222 of the furnace. In a case where an operation for removing the protection tube 202c is input from the operation board 310c to the electric motor 350c, the electric motor 350c is rotated in a direction in which the protection tube 202c is moved to the outside 228 of the furnace.

Here, an operation in a case where the protection tube 202c of the furnace monitoring device 200c of the above-described third embodiment is removed from the gasifier 101. First, an operator operates the operation board 310c to rotate the electric motor 350c, and thus, the protection tube 202c is moved to the outside 228 of the furnace.

Next, the operator operates the operation board 310c so as to close the valve 302c. Next, the operator opens the valve 316c, and thus, the pressure inside the first pipe 304c is decreased by the depressurizing device 312c, and the depressurization is performed. Next, the operator confirms that the pressure gauge 314c pressure is at atmospheric pressure. Next, the operator opens a manhole (not shown) formed in the cylindrical vessel 308c to cool the protection tube 202c. After the operator confirms that the protection tube 202c is sufficiently cooled, the operator removes the protection tube 202c from the cylindrical vessel 308c.

Next, an operation in a case where the protection tube 202c of the furnace monitoring device 200c of the above-described third embodiment is inserted into the gasifier 101 will be described. First, an operator opens the manhole (not shown) formed in the cylindrical vessel 308c. Next, the operator attaches the protection tube 202c to a portion inside the cylindrical vessel 308c. Next., the operator closes the manhole (not shown) formed in the cylindrical vessel 308c. Next, the operator operates the operation board 310c to rotate the electric motor 350c, and thus, the protection tube 202c is moved to the inside 222 of the furnace, and the protection tube 202c is inserted in front of the valve 302c. Next, the operator operates the operation board 310c to open the valve 302c. Next, the operator operates the operation board 310c to rotate the electric motor 350c, and thus, the protection tube 202c is moved to the inside 222 of the furnace, and the protection tube 202c is inserted to a predetermined position.

The furnace monitoring device 200c according to the third embodiment includes the inserting and removing device 300c. Accordingly, even in a case where trouble occurs in the furnace monitoring device 200c during the operation of the gasification unit 14 and maintenance is required, it is possible to attach the furnace monitoring device 200c to the gasification unit 14 or to detach the furnace monitoring device 200c from the gasification unit 14 without stopping the gasification unit 14, and it is possible to improve an operation rate of the gasification unit 14.

In addition, the furnace monitoring device 200c of the third embodiment includes the first ball screw mechanism 320c and the second ball screw mechanism 330c. However, the present invention is not limited to this. For example, the number of the ball screw mechanisms may be one or three more.

Hereinbefore, the present invention is described with reference to the above embodiments. However, the technical scope of the present invention is not limited to the scopes described in the above embodiments. Various modifications or improvements can be added to the above-described embodiments within a scope not deviating from the gist of the invention, and an aspect added with the modifications or improvements is also included in the technical scope of the present invention. In addition, the plurality of embodiments may be combined.

For example, the inserting and removing device 300c may be applied to the furnace monitoring device 200a.

REFERENCE SIGNS LIST

10: integrated coal gasification combined cycle (integrated gasification combined cycle)
11: coal supply unit
11a: coal supply line
14: gasification unit
15: char recovery unit
16: gas clean-up unit
17: gas turbine
18: steam turbine
19: generator
20: heat recovery steam generator
41: compressed air supply line
42: air separation unit
43: first nitrogen supply line
45: second nitrogen supply line
46: char return line
47: oxygen supply line
48: foreign matter removal unit
49: gas generation line
51: dust collection unit
52: supply hopper
53: gas discharge line
61: compressor
62: combustor
63: turbine
64: rotary shaft
65: compressed air supply line
66: fuel gas supply line
67: combustion gas supply line
68: booster
69: turbine
70: flue gas line
71: steam supply line
72: steam recovery line
73: condenser
74: gas purifying unit
79: stack
101: gasifier
102: syngas cooler
111: pressure vessel
111: gasifier wall
115: annulus portion
116: combustor portion
117: diffuser portion
118: reductor portion
121: gas discharge port
122: slag hopper
125: gasifier outlet gas thermometer
126, 127: burner
178, 129: burner inlet cutoff valve
130: control means
131: heat exchanger (evaporator)
132: heat exchanger (superheater)
134: heat exchanger (economizer)
200a, 200b, 200c: furnace monitoring device
202a, 202b, 202c: protection tube
204a, 204b: outer cylinder
206a, 206b: fluid passage
208a, 208b: inner cylinder
212a, 212b, 212c: nozzle
214a, 214b, 230a, 230b, 244b: flange portion
216a, 216b, 234b, 236b: boss
218a: air source valve
220a, 220b: air supply source
222: inside of furnace
224a: opening
226a: ejection hole
228: outside of furnace
232a: closing flange
238b: cooling water supply system
240b: cooling water recovery system
242b: fiber pressure resistance tube
246b: fiberscope
240b: transparent window
250a: monitoring window
252a: imaging means
254a: imaging device
256a: optical filter
258a optical filter switching unit
259a: lighting device
260a: optical axis
262a, 266b: support member
264b: mirror
268b: cap
270b: fluid passage
272b: infrared thermometer
300c: inserting and removing device
302c: valve
304c: first pipe
306c: second pipe
308c: cylindrical vessel
310c: operation board
312c: depressurizing device
314c: pressure gauge
316c: valve
318c: seal member
320c: first ball screw mechanism
322c: first screw shaft 324c: first nut
326c: first gear
328c: first support member
330c: second ball screw mechanism
332c: second screw shaft
334c: second nut
336c: second gear
338c: second support member
350c: electric motor
352c: shaft
354c: third gear

The invention claimed is:

1. A furnace monitoring device which monitors an inside of a gasifier through which a combustible gas flows, comprising:
    a nozzle which is inserted into the gasifier, is fixed to the gasifier, and has an internal cavity;
    a protection tube which is formed in a tubular shape, is inserted into the nozzle, and has a blocked portion which is positioned inside the gasifier;
    a monitoring window which is provided on a portion of the protection tube inside the gasifier and transmits light;
    a purge mechanism which supplies a gas including an oxygen containing gas to a surface of the monitoring window inside the gasifier; and
    imaging means for imaging the inside of the gasifier via the monitoring window,
    wherein the imaging means includes an imaging device which images the inside of the gasifier via the monitoring window, an optical filter which shields a wavelength of light emitted from a radical, and an optical filter switching unit which attaches the optical filter to the imaging device or detaches the optical filter from the imaging device, and
    wherein the optical filter transmits only a wavelength within a range from 759 nm to 928 nm;
    the furnace monitoring device further comprising control means which is connected to the optical filter switching unit,
    wherein the control means attaches the optical filter to the imaging device in a case where a gas discharge temperature of the gasifier exceeds a preset value or a fuel is introduced into the gasifier, and
    wherein the control means detaches the optical filter from the imaging device in a case where the gas discharge temperature of the gasifier is equal to or less than the preset value and the fuel is not introduced into the gasifier.

2. The furnace monitoring device according to claim 1, further comprising:
    a lighting device which illuminates the inside of the gasifier via the monitoring window.

3. The furnace monitoring device according to claim 1, further comprising:
    a valve which is attached to the nozzle and shields the inside and an outside of the gasifier;
    a cylindrical vessel which is connected to the nozzle and shields a periphery of the protection tube from an outside; and
    a movement mechanism which moves the protection tube with respect to the cylindrical vessel.

4. A gasification unit comprising:
    the furnace monitoring device according to claim 1.

* * * * *